025921962A

United States Patent [19]
Kriesel et al.

[11] Patent Number: 5,921,962
[45] Date of Patent: Jul. 13, 1999

[54] FLUID DELIVERY DEVICE WITH FLOW INDICATOR AND RATE CONTROL

[75] Inventors: Marshall S. Kriesel, St. Paul; Farhad Kazemzadeh, Bloomington; Matthew B. Kriesel, St. Paul, all of Minn.; William W. Feng, Lafayette, Calif.; Steve C. Barber, Shorewood, Minn.; William J. Kluck, Hudson, Wis.

[73] Assignee: Science Incorporated, Bloomington, Minn.

[21] Appl. No.: 08/991,122

[22] Filed: Dec. 16, 1997

Related U.S. Application Data

[63] Continuation-in-part of application No. 08/606,090, Feb. 23, 1996, Pat. No. 5,779,676, which is a continuation-in-part of application No. 08/541,184, Oct. 11, 1995, Pat. No. 5,776,103.

[51] Int. Cl.⁶ .................................................. A61M 37/00
[52] U.S. Cl. ...................... 604/132; 604/246; 604/890.1; 128/DIG. 12
[58] Field of Search ..................................... 604/131, 132, 604/151, 153, 890.1, 246; 128/DIG. 12

[56] References Cited

U.S. PATENT DOCUMENTS

| | | | |
|---|---|---|---|
| 4,193,397 | 3/1980 | Tucker et al. | 604/83 |
| 4,474,575 | 10/1984 | Eckenhoff et al. | 604/131 |
| 4,668,231 | 5/1987 | DeVries et al. | 604/891 |
| 4,968,301 | 11/1990 | DiPalma et al. | 604/132 |
| 4,969,873 | 11/1990 | Steinbach et al. | 604/93 |

*Primary Examiner*—Corrine McDermott
*Attorney, Agent, or Firm*—James E. Brunton

[57] ABSTRACT

A fluid delivery device for infusing medicinal fluids having a self-contained stored energy membrane for expelling fluids at a precisely controlled rate. The device is of a compact, low profile, laminate construction so that it can conveniently be used for the fluids, such as insulin and the like, into an ambulatory patient at controlled rates over extended periods of time. Included within the device are various fluid flow control elements including a unique hydraulic fluid rate control system for ultra low flow delivery. Also included is a highly novel flow indictor for providing a positive indication of fluid flow from the device and for indicating at any given time the amount of fluid remaining in the device.

24 Claims, 10 Drawing Sheets

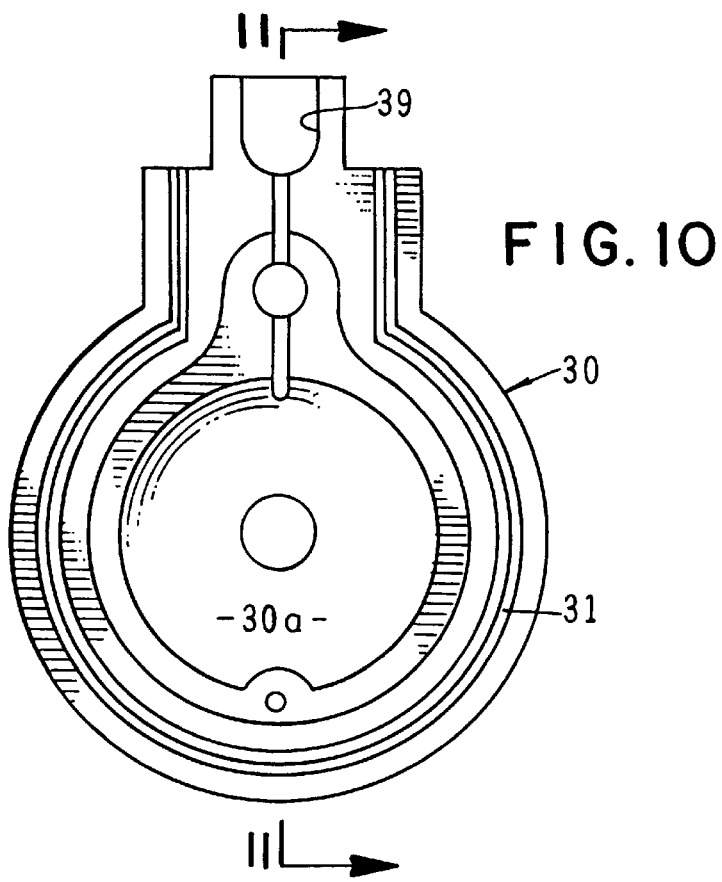
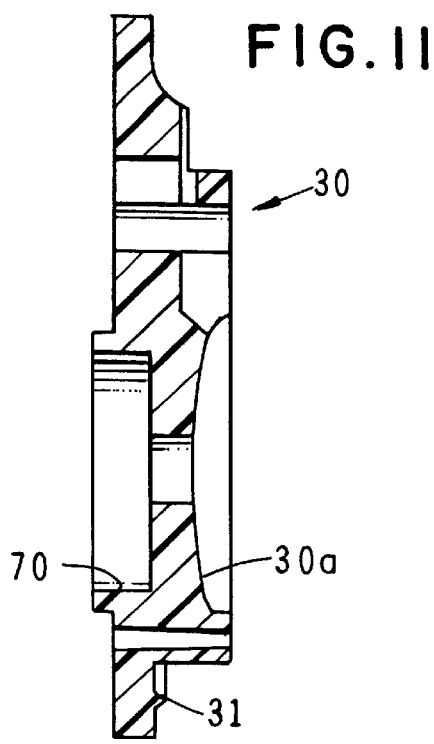
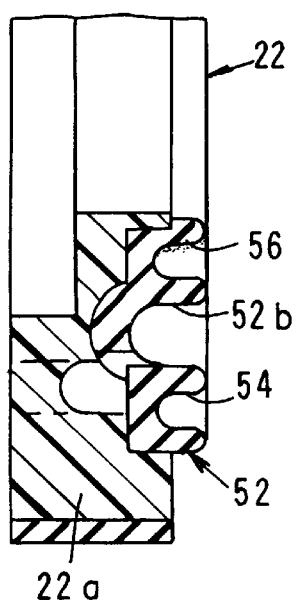
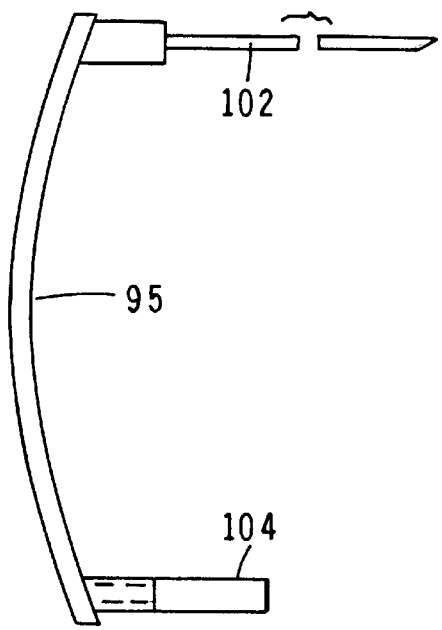
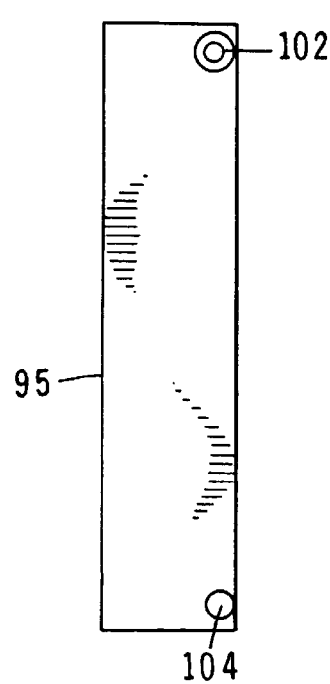

FLUID DELIVERY DEVICE WITH FLOW INDICATOR AND RATE CONTROL

This is a Continuation-In-Part application of U.S. Ser. No. 08/606,090 filed Feb. 23, 1996 now U.S. Pat. No. 5,779,676, which is a Continuation-In-Part of application, U.S. Ser. No. 08/541,184, filed Oct. 11, 1995 now U.S. Pat. No. 5,776,103.

BACKGROUND OF THE INVENTION

1. Field of the Invention

The present invention relates generally to fluid delivery devices. More particularly, the invention concerns an improved fluid delivery apparatus for precise subdermal delivery over time of medicinal liquids to an ambulatory patient, the device including novel fluid flow control and flow indicator means.

2. Discussion of the Prior Art

A number of different types of liquid dispensers for dispensing medicaments to ambulatory patients have been suggested. Many of the devices seek either to improve or to replace the traditional hypodermic syringe which has been the standard for delivery of liquid medicaments such as insulin solution.

Those patients that require frequent injections of the same or different amounts of medicament, find the use of the hypodermic syringe both inconvenient and unpleasant. Further, for each injection, it is necessary to first draw the injection dose into the syringe, then check the dose and, after making certain that all air has been expelled from the syringe, finally, inject the dose. This cumbersome and tedious procedure creates an unacceptable probability of debilitating complications, particularly for the elderly and the infirm.

One example of the urgent need for an improved liquid delivery device for ambulatory patients can be found in the stringent therapeutic regimens used by insulin-dependent diabetics. The therapeutic objective for diabetics is to consistently maintain blood glucose levels within a normal range much as the normally functioning pancreas would do by secreting a very low level of extremely fast-acting insulin at a basal rate into the blood stream throughout the day and night.

Consider the normal individual who doesn't have diabetes. A normal individual's cells require energy throughout the day just to maintain a basal metabolic rate. This energy is supplied to the cells by glucose that is transported from the bloodstream to the cells by insulin. When food is consumed, the blood glucose level rises and the pancreas responds by releasing a surge of fast-acting insulin. To mimic this natural process with individual injections, the individual would have to administer minuscule amounts of fast-acting insulin every few minutes throughout the day and night.

Conventional therapy usually involves injecting, separately, or in combination, fast-acting and slower-acting insulin by syringe several times a day, often coinciding with meals. The dose must be calculated based on glucose levels present in the blood. Slower-acting insulin is usually administered in the morning and evening to take advantage of longer periods of lower level glucose uptake. Fast-acting insulin is usually injected prior to meals. If the dosage of fast-acting insulin is off, the bolus administered may lead to acute levels of either glucose or insulin resulting in complications, including unconsciousness or coma. Over time, high concentrations of glucose in the blood can also lead to a variety of chronic health problems, such as vision loss, kidney failure, heart disease, nerve damage, and amputations.

A recently completed DCCT (Diabetes Control and Complications Trial) study sponsored by the National Institutes of Health (NIH) investigated the effects of different therapeutic regimens on the health outcomes of insulin-dependent diabetics. This study revealed some distinct advantages in the adoption of certain therapeutic regimens. Intensive therapy that involved intensive blood glucose monitoring and more frequent administration of insulin by conventional means, for example, syringes, throughout the day saw dramatic decreases in the incidence of debilitating complications.

The NIH study also raises the question of practicality and patient adherence to an intensive therapy regimen. A bona fide improvement in insulin therapy management must focus on the facilitation of patient comfort and convenience as well as dosage and administration schemes. Basal rate delivery of insulin by means of a convenient and reliable delivery device over an extended period of time represents one means of improving insulin management. Basal rate delivery involves the delivery of very small volumes of fluid (for example, 0.3–3 mL. depending on body mass) over comparatively long periods of time (18–24 hours). As will be appreciated from the discussion which follows, the apparatus of the present invention is uniquely suited to provide precise fluid delivery management at a low cost in those cases where a variety of precise dosage schemes are of utmost importance.

An additional important feature of the apparatus of the present invention is the provision of a novel hydraulic rate control means for precisely controlling the rate of flow of fluid from the device by controlling the rate of flow between the ullage compartments of the device as the distended energy membrane returns to its less distended configuration.

Another feature of the improved apparatus of the invention comprises the provision of novel fluid flow indicator means for positively indicating flow of fluid from the device.

Because the embodiments of the invention described herein comprise improvements to the devices described in U.S. Ser. No. 08/606,090 filed Feb. 23, 1997, application Ser. No. 08/606,090 is hereby incorporated by reference in its entirety as though fully set forth herein.

Also relative to a complete understanding of the present invention is an earlier filed application by the present inventor, which is identified by the Ser. No. 08/541,184. This application, which was filed on Oct. 11, 1995 is also incorporated by reference in its entirety as though fully set forth herein.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly. The ullage in these devices is provided in the form of a semi-rigid structure having flow channels leading from the top of the structure through the base to inlet or outlet ports of the device.

In the rigid ullage configuration described in U.S. Pat. No. 5,205,820, the stored energy means of the device must be superimposed over the ullage to form the fluid-containing reservoir from which fluids are expelled at a controlled rate by the elastomeric membrane of the stored energy means tending to return to a less distended configuration in the direction toward the ullage. With these constructions, the stored energy membrane is typically used at higher extensions over a significantly large portion of the pressure-deformation curve.

For good performance, the elastomeric membrane materials selected for construction of the stored energy membrane must have good memory characteristics under conditions of extension; low stress relaxation; good resistance to chemical and radiological degradation; and appropriate gas permeation characteristics depending upon the end application to be made of the device. Once an elastomeric membrane material is chosen that will optimally meet the desired performance requirements, there still remain certain limitations to the level of refinement of the delivery tolerances that can be achieved using the rigid ullage configuration. These result primarily from the inability of the rigid ullage to conform to the changing geometry of the elastomeric membrane near the end of the delivery period. This nonconformity can lead to extended delivery rate tail-off and higher residual problems when extremely accurate delivery is required. For example, when larger volumes of fluid are to be delivered, the tail-off volume represents a smaller portion of the fluid amount delivered and therefore exhibits much less effect on the total fluid delivery profile, but in very small dosages, the tail-off volume becomes a larger portion of the total volume. This sometimes places severe physical limits on the range of delivery profiles and system flow rate linearity tolerance that may easily be accommodated using the rigid ullage configuration. An additional penalty inherent in rigid ullage construction is the high Z axis height of the ullage that will be required to maintain acceptable flow rate delivery tolerance and tail off delivery requirements.

As will be better appreciated from the discussion which follows, the apparatus of the present invention provides a unique and novel improvement for a disposable dispenser of simple but highly reliable construction that may be adapted to many applications of use. A particularly important aspect of the improved apparatus is the incorporation of a secondary hydraulic rate control means and the use of conformable ullages made of flowable materials such as oils which uniquely conform to the continuously changing geometry of the stored energy membrane during the delivery cycle. This novel construction will satisfy even the most stringent delivery tolerance requirements and elegantly overcomes the limitation of materials selection. For a further discussion of the advantages of the use of conformable ullages, reference should be made to U.S. Pat. No. 5,656,032. Because of the pertinence of this patent, which was issued to the present inventors, it is hereby incorporated by reference as through fully set forth herein.

Another useful liquid delivery device is that described in U.S. Pat. No. 5,226,896 issued to Harris. This device comprises a multidose syringe having the same general appearance as a pen or mechanical pencil. the device is specifically adapted to provide for multiple measured injections of materials such as insulin or human growth hormones.

Still another type of liquid delivery device is disclosed in U.S. Pat. No. 4,592,745 issued to Rex et al. This device is, in principle, constructed as a hypodermic syringe, but differs in that it enables dispensing of a predetermined portion from the available medicine and in that it dispenses very accurate doses.

The present invention seeks to significantly improve over the prior art by providing a novel fluid delivery device having two interconnected fluid reservoirs, which is low in profile, is compact, is easy to use by ambulatory patients, and is eminently capable of meeting the most stringent of fluid delivery and flow rate linearity tolerance requirements.

SUMMARY OF THE INVENTION

It is an object of the present invention to provide an apparatus having a self-contained stored energy membrane for expelling fluids at a precisely controlled rate which is of a compact, extremely low profile, laminate construction. More particularly, it is an object of the invention to provide such an apparatus which is of very low profile so that it can conveniently be used for the precise delivery of pharmaceutical fluids, such as insulin solution and the like, into an ambulatory patient at controlled ultra slow flow delivery rates over extended periods of time.

It is another object of the invention to provide an apparatus of the aforementioned character which is highly reliable and easy-to-use by lay persons in a non-hospital environment.

Another object of the invention is to provide an apparatus which embodies a conformable mass which defines an ullage within the reservoirs of the device which will closely conform to the shape of the stored energy membrane thereby effectively avoiding extended flow delivery rate tail-off at the end of the fluid delivery period and thus precisely controls the time of delivery.

A further object of the invention is to provide a low profile, fluid delivery device of laminate construction which can meet even the most stringent fluid delivery tolerance requirements.

Another object of the invention is to provide an apparatus of the character described in the preceding paragraphs which includes a novel hydraulic flow rate control means for precisely controlling the rate of fluid flow from the device.

Another object of the invention is to provide an apparatus of the class described which further includes a novel fluid flow indicator for providing a positive indication of fluid flow from the device.

Another object of the invention is to provide an apparatus of the character described which, due to its unique construction, can be manufactured inexpensively in large volume by automated machinery.

Other objects of the invention are set forth in the copending United States applications which are incorporated herein by reference and still further objects will become apparent from the discussion which follows.

BRIEF DESCRIPTION OF THE DRAWINGS

FIG. 10 is a view taken along lines 10—10 of FIG. 6.

FIG. 11 is a cross-sectional view taken along lines 11—11 of FIG. 10.

FIG. 12 is a cross-sectional view taken along lines 12—12 of FIG. 9.

FIG. 13A is top plan view of the back plate of the flow indicator assembly of the invention.

FIG. 13B is a rear view of the indicator assembly back plate shown in FIG. 13A.

DESCRIPTION OF THE INVENTION

Figure 1:
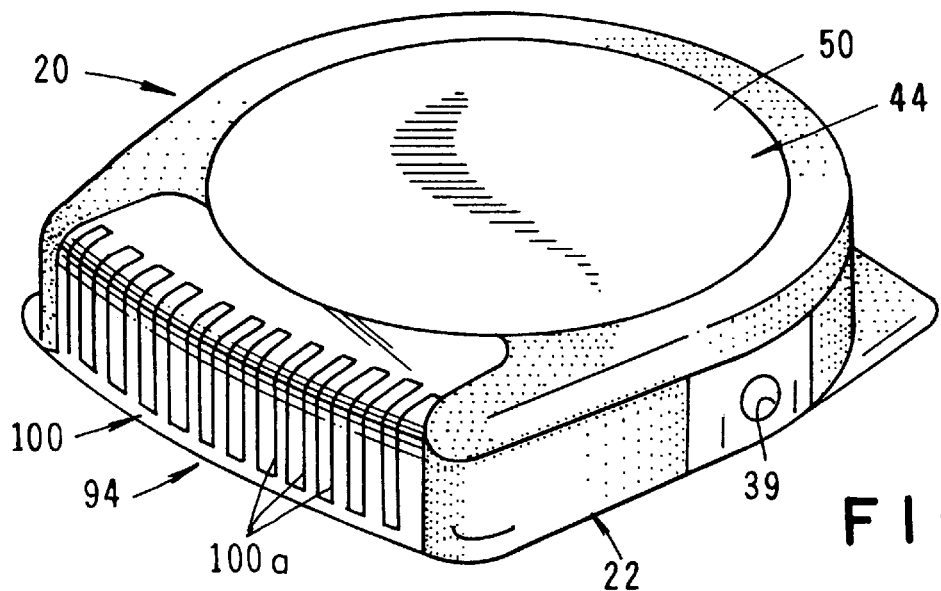
FIG. 1 is a generally perspective view of one form of the fluid delivery portion of the device of the present invention.
Figure 2:
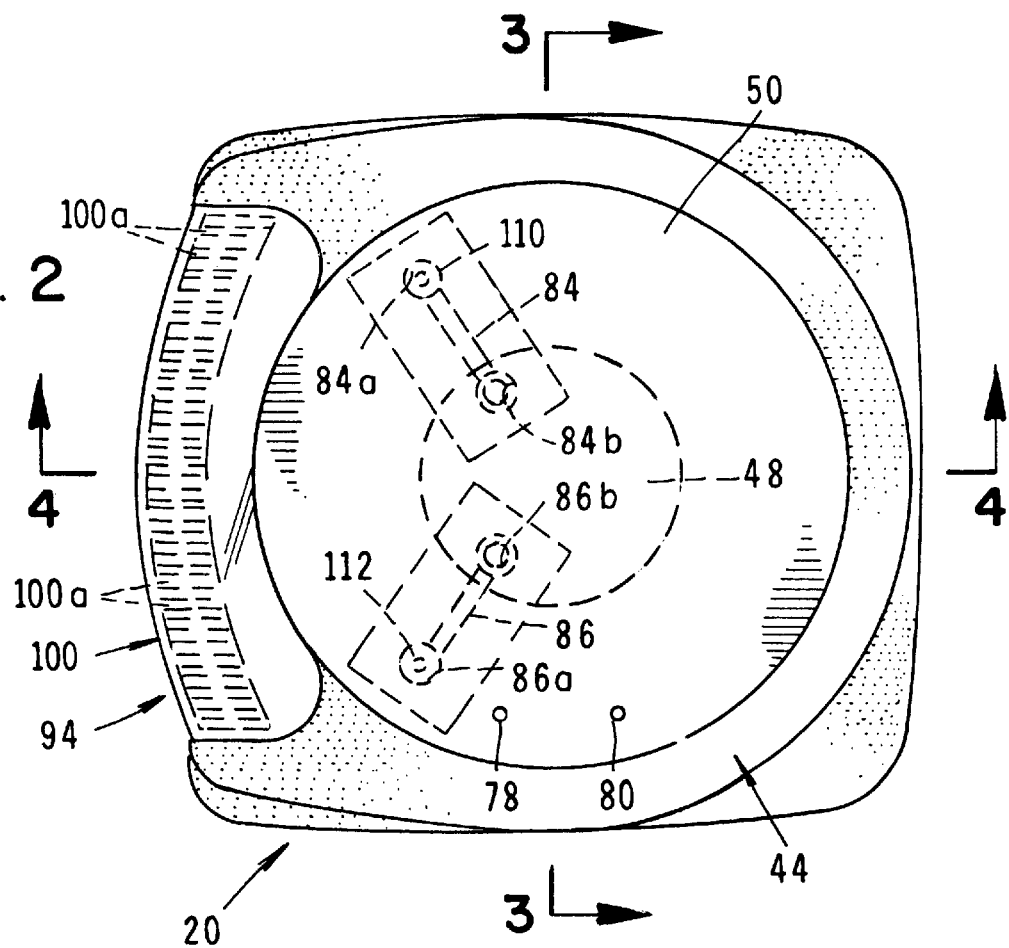
FIG. 2 is a top plan view of the device shown in FIG. 1.
Figure 3:
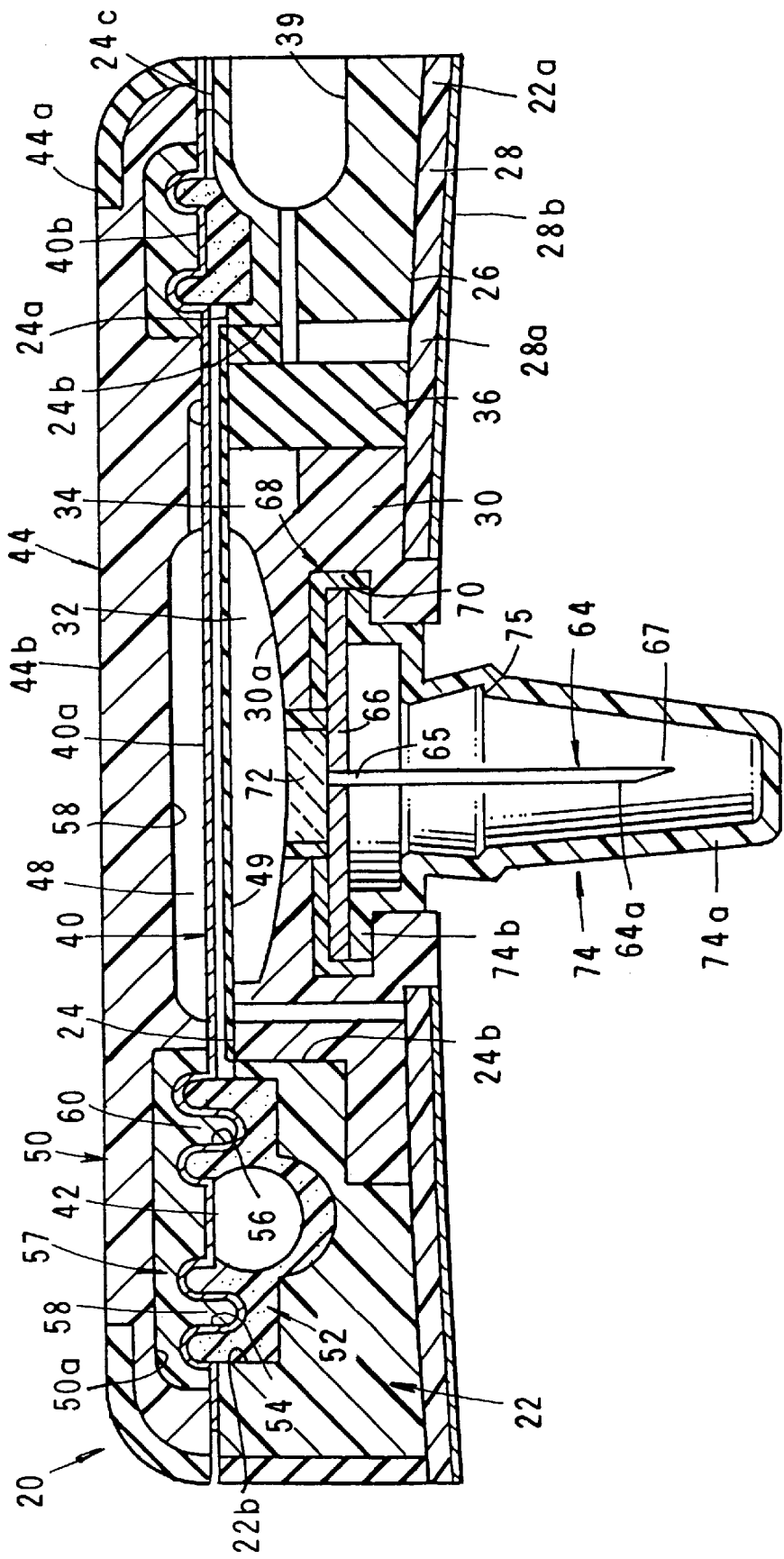
FIG. 3 is an enlarged, cross-sectional view taken along lines 3—3 FIG. 2.
Figure 4:
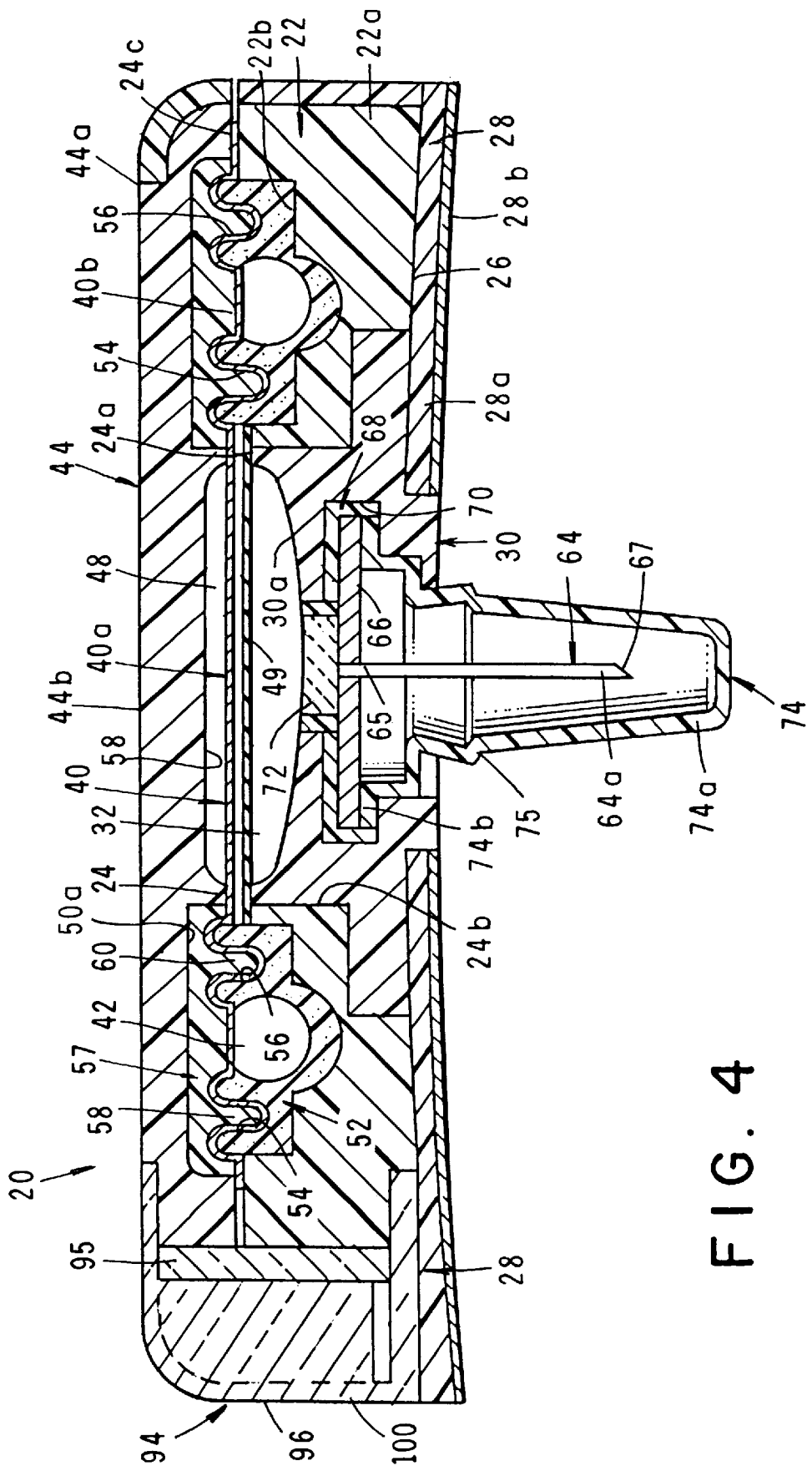
FIG. 4 is an enlarged cross-sectional view taken along lines 4—4 of FIG. 2.

Referring to the drawings and particularly to FIGS. 1 through 5, one form of the fluid delivery device of the present invention is there shown and generally designated by the numeral 20. This device, which is specially designed for sub dermal infusion of selected medicaments, comprises a base assembly 22 including a base component 22a having an upper surface 24 including a central portion 24a having an opening 24b (FIG. 5) and a peripheral portion 24c circumscribing central portion 24a. As best seen in FIGS. 3 and 4, base assembly 22 is also provided with a lower surface 26 to which a patient interconnection means or adhesive pad assembly 28 is connected (FIG. 3). As will be described more fully hereinafter, pad assembly 28, which includes a foam pad 28a and a peel strip 28b, functions to releasably interconnect the device to the patient so as to hold it securely in place during the medicament delivery step.

An infusion means, which includes a reservoir defining housing 30 that is receivable within opening 24b of base component 22a, functions to controllably deliver medicament to the patient when the device is operatively affixed to the patient. The details of the construction of this important infusion means will be discussed more fully in the paragraphs which follow.

Figure 15:
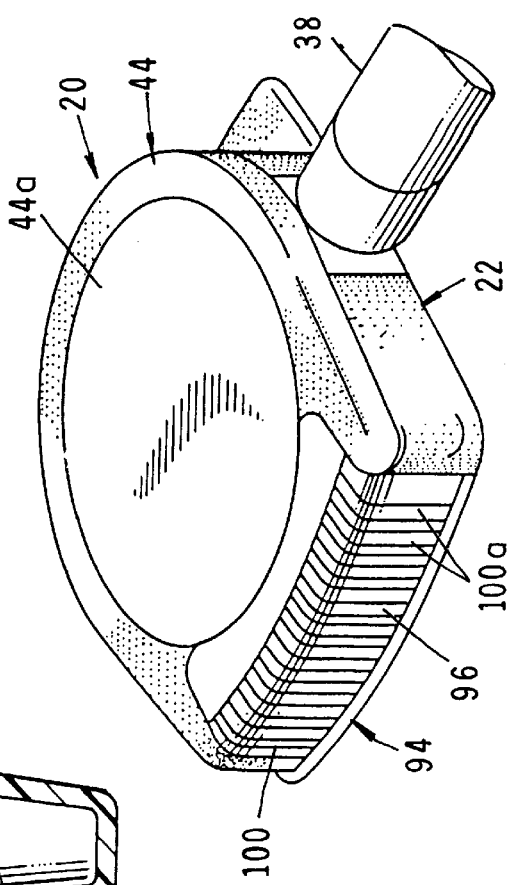
FIG. 15 is a generally perspective view of the device similar to FIG. 1 but showing the fill means of the invention interconnected with the fluid delivery portion of the device.

A stored energy means overlays the upper surface 24 of base assembly 22 and cooperates with housing 30 to form a central medicinal fluid reservoir 32. Reservoir 32 has an inlet port 34 (FIG. 3) which communicates, via a pierceable septum 36, with a filling means shown here as a filling syringe 38 which is partially receivable within a fill opening 39 formed in base assembly 22 (see FIG. 15 and 16). The stored energy means is here provided in the form of at least one distendable membrane 40 which is superimposed over base assembly 22. Membrane 40, which is distendable as a result of pressure imparted on the membrane by fluids introduced into the reservoirs of the device, includes a central portion 40a and a peripheral portion 40b. As membrane 40 is distended in the manner shown in FIG. 16, substantial internal stresses will be established in the peripheral portion 40b of the membrane, which stresses tend to move the membrane toward a less distended configuration and in a direction toward its starting position as shown in FIG. 3. For reasons to be discussed later, filling of the reservoir in the manner shown in FIG. 16 will prestress the central portion 40a of the membrane a predetermined amount. It is to be understood that membrane 40 can be constructed from a single membrane or from multiple membranes joined together to form a laminate construction.

As best seen in FIG. 3, the central portion of membrane 40 cooperates with a surface 30a of housing 30 to form the expandable and contractable central medicinal fluid reservoir 32. The peripheral portion of membrane 40 also cooperates with base assemblage 22 to form an indicator fluid reservoir 42, the character and purpose of which will be more fully described hereinafter.

Superimposed over and sealably connected to base assembly 22 by any suitable means such as sonic welding is a cover assembly 44. As best seen by referring to FIG. 14, the peripheral portion 44a of cover assembly 44 cooperates with the peripheral portion of membrane 40 to form a peripheral, generally toroidal-shaped, conformable ullage reservoir 46. Similarly, the central portion 44b of cover assembly 44, cooperates with the central portion of membrane 40 to form a central conformable ullage reservoir 48. Disposed within reservoirs 46 and 48 is the novel ullage defining means of the invention which here comprises a flowable mass, such as an oil. In a manner presently to be described, this flowable mass is acted upon by the distendable membrane as the membrane, after being distended by the filling of reservoir 46, tends to return to its less distended configuration. As the peripheral portion of the distendable membrane tends to return to its less distended configuration due to internal stresses formed within the peripheral portions of the membrane during the ullage fill step, the ullage oil contained within reservoir 46 will be urged to flow uniformly outwardly of reservoir 46 and into central reservoir 48.

Figure 5:
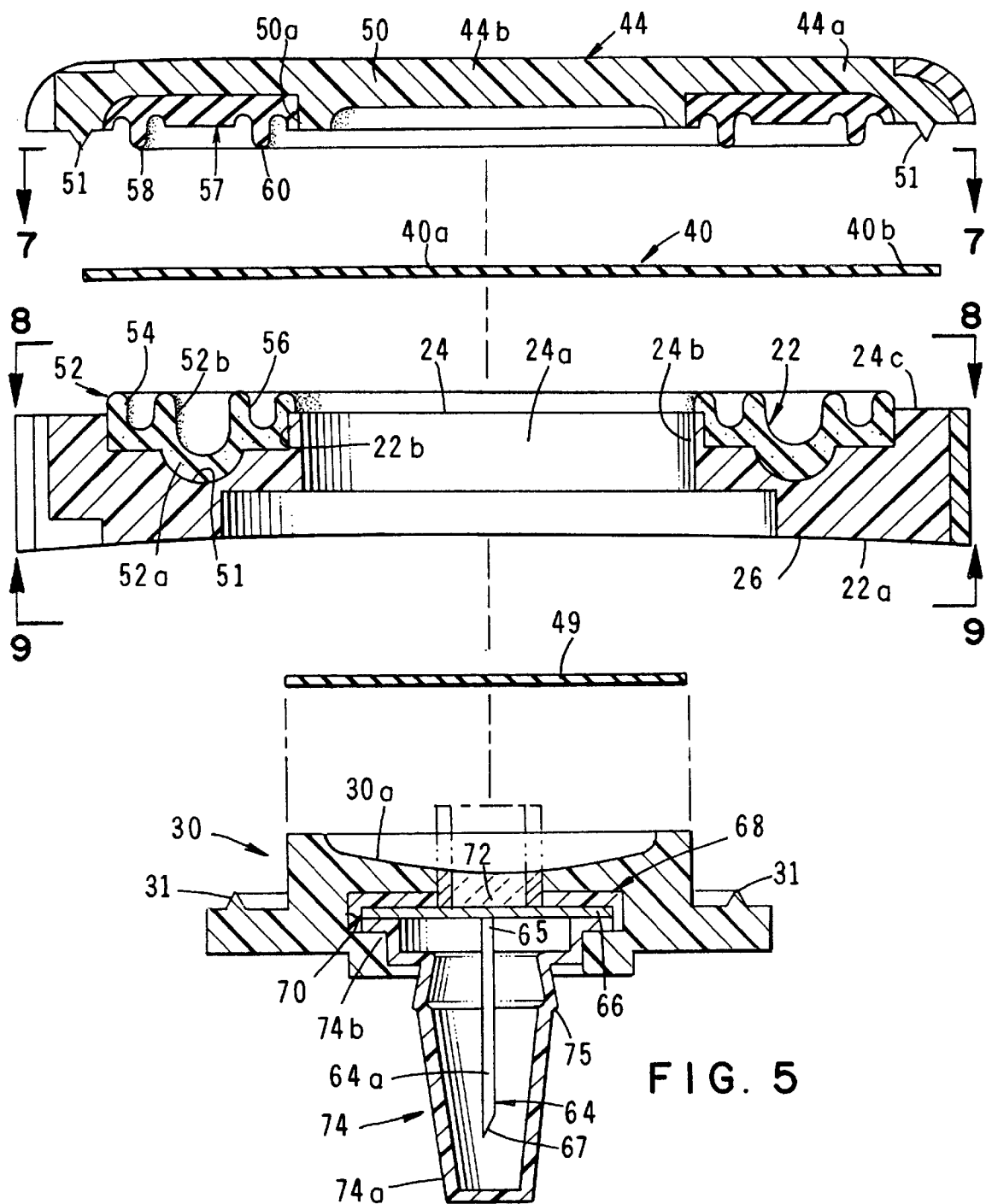
FIG. 5 is an exploded, cross-sectional view of the device shown in FIG. 4.

As best seen in FIGS. 3, 4, and 5 a barrier member 49 is disposed between the central portion of the distendable membrane 40 and a surface 30a of housing 30. During the medicinal fluid filling step illustrated in FIG. 16, the fluid introduced through inlet port 34 of the medicinal fluid reservoir will impinge first upon barrier member 49. The barrier member will, in turn, act upon the central portion of the prestressed distendable membrane 40 causing it to distend toward cover 44 in the manner shown in FIG. 16.

Cover assembly 44 includes a rigid cover member 50, which having a generally circular energy director 51 (FIG. 5) expedites the sonic welding of cover 50 to base assembly 22. sealing means are provided to sealably connect cover 50 to base assembly 22. These novel sealing means here comprise a first elastomeric insert 52 which forms a part of base assembly 22. As best seen in FIGS. 3 and 5, insert 52 is provided with circular grooves 54 and 56. Also forming a part of the sealing means is an elastomeric insert 57 which forms a part of cover assembly 44. Insert 57 is provided with generally circular-shaped protuberances 58 and 60. As best seen in FIG. 3, protuberance 58 is sealably receivable within groove 54 of insert 52, while protuberance 60 is sealably received in groove 56 of insert 52. As shown in FIGS. 3 and 4, protuberance 58 and 60 function to sealably clamp distendable membrane 40 between the cover and base assemblies. Inserts 52 and 57 are preferably formed from a suitable elastomeric material which, in a manner well understood by those skilled in the art, is injected into circular shaped cavities 22b and 50a formed in base assembly 22 and cover 50 respectively. It is to be noted that cavity 22b includes a semicircular shaped groove 51 which receives a semicircular protuberance 52a formed on insert 52 (FIG. 5). Insert 52 also includes a generally toroidal shaped cavity 52b which, along with membrane 40, forms the previously mentioned indicator fluid reservoir 42.

Elastomers suitable for forming inserts 52 and 57 include any non-coring elastomeric material, including silicones, polyolyfins and other TPE rubbers. With respect to the distendable membrane 40 and the barrier membrane 49, these important components can be constructed from a number of different materials including rubbers, plastics and other thermoplastic elastomers. These include latex rubber, polyisoprene (natural rubber), butyl rubber, nitrile rubber, other homopolymer, copolymers (random, alternating, block, graft, crosslink and starblock), mechanical polyblends and interpenetrating polymer networks.

Manufacturers of materials suitable for use in construction of the distendable membrane and the barrier membrane include Dow Chemical, General Electric, B.P. Polymers, Mobay Chemical, Shell Oil Corp., Petrarch Systems, DuPont, Concept Polymers, Goodyear, and Union Carbide Corp.

With respect to the ullage defining means, the flowable material can be selected from a variety of viscous fluids. Fluids such as water, mineral oil, peanut oil, silicone oil, glycerine, and methyl cellulose can be used. The choice of fluid is, in part, determined by the fluid viscosity centipoise requirements needed to achieve the desired rate of delivery, and in part, by the material used to construct the distendable membrane.

Examples of material found to be particularly well suited for the ullage defining means includes fluorinated oils. Fluorinated oils are extremely pure and stable, and therefore they are nonreactive with the elastomers that can be used to construct the distendable membrane of the current invention. Fluorinated oils are also available in a range of viscosities suitable to this application.

An example of fluorinated oil suitable for use as the ullage defining means is available from DuPont and is sold under the name and style KRYTOX.

With respect to the structural cover 50 and base assembly 22, these components can also be produced from a variety of materials including one of several polymer groups. The degree of hardness of these materials can range from soft, resilient or rigid, and the following polymers can be employed: Polypropylene (PP), Ultra high molecular weight polyethylene (UHMW PE), High density polyethylene (HDPE), Polyvinylidene Fluoride (PVDF), Ethylene-vinyl acetate (EVA), Styrene Acrylonitrile (SAN), Polytetrafluoroethylene (PTFF). A suitable source of these materials is Porex Technologies of Fairburn, Georgia. It is to be understood that other suitable materials well known to those skilled in the art can also be used, including a material sold by B.P Chemicals International of Cleveland, Ohio, under the name and style "Barex". This material is a clear rubber modified Acroylonitrile Copolymer which has wide application in the packaging industry because of its superior gas barrier, chemical resistance and extrusion (thermoforming) and injection molding capabilities.

The foam pad adhesive 28a and peel strip 28b is preferably composed of a thin (1/32") 30 mil closed cell polyethylene (PE) foam double coated with a non-sensitizing acrylic pressure sensitive adhesive (PSA), and 90 lb. white polyethylene coated release liner (peel strip). This foam is also available in 1/16 inch and 1/8 inch thickness. The foam is stretchable, soft, elastically conformable, cushioning, hypoallergenic, and is desirable for application where sustained use is required. The material is available from the 3M Company of Saint Paul, Minn. and from Betham Corporation of Middlesex, N.J.

Figure 6:
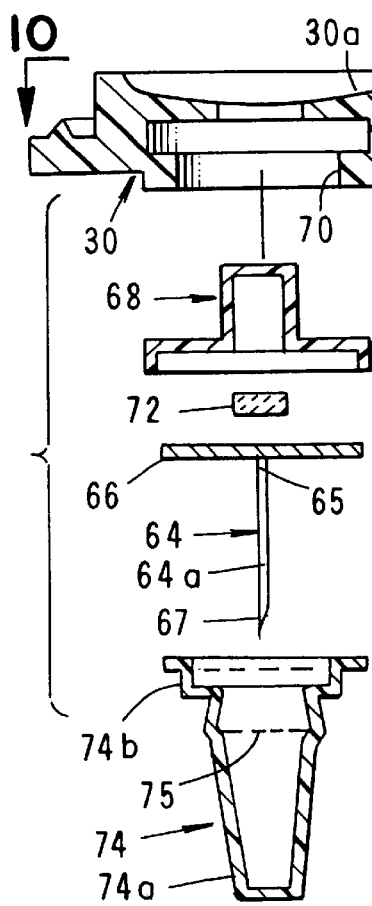
FIG. 6 is an exploded, cross-sectional view of one form of the infusion means of the device which comprises the lower assembly shown in FIG. 5.

Referring particularly to FIGS. 3, 5, and 6, the infusion means of this latest form of the invention for subdermal infusion of medicaments into the patient, can be seen to include, in addition to reservoir defining housing 30, a downwardly extending hollow cannula 64 which is carried by a disk-like support member 66. Support member 66 is closely received within a cannula assembly housing 68 which, in turn, is closely received within a cavity 70 formed in reservoir defining housing 30. Hollow cannula 64 includes a body portion 64a having an inlet end 65, and an outlet end 67 formed in a needle-like segment which extends generally perpendicularly downward from the lower surface of base assembly 22. Disposed between inlet end 65 of cannula 64 and medicament reservoir 32 is an impedance frit 72 which forms a part of the flow control means of the invention for controlling fluid flow from reservoir 32 toward the patient. To protect cannula 64 from damage, a protective cover 74 surrounds the cannula. At time of use, the skirt portion 74a of the protective cover 74 can be readily separated from the base portion 74b of the cover by breaking it away along a serration line 75 formed between the skirt portion 74a and the base portion 74b.

Figure 7:
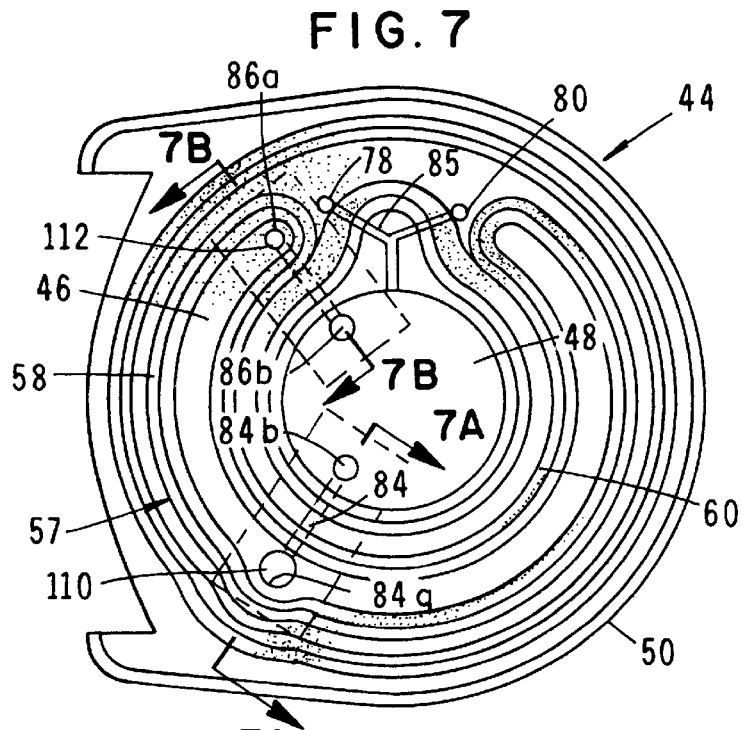
FIG. 7 is a view taken along lines 7—7 of FIG. 5.
Figure 14:
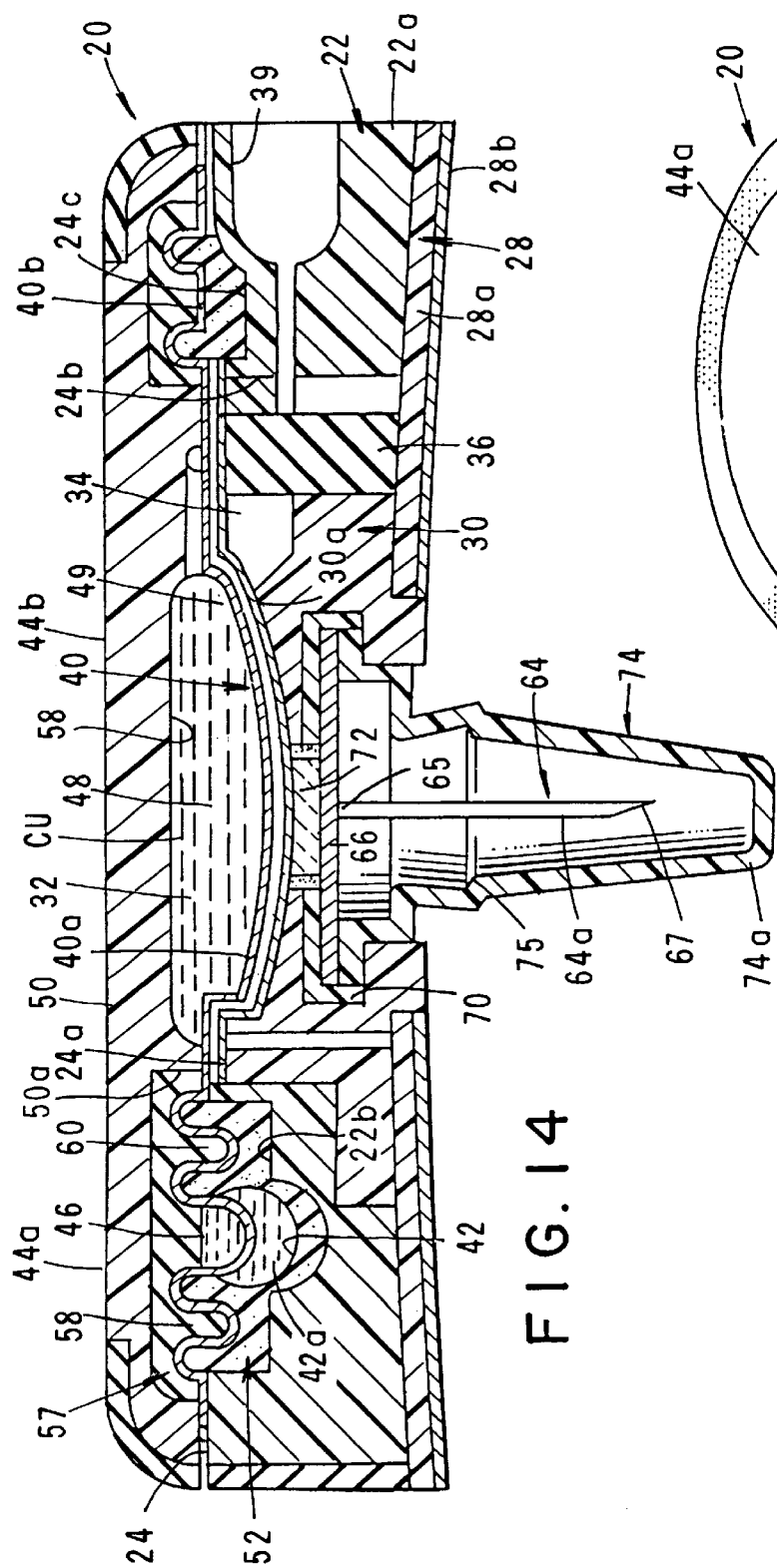
FIG. 14 is a cross-sectional view similar to FIG. 3 but showing the centrally disposed reservoir and toroidal chamber of the device filled with a flowable liquid that comprises the ullage defining means of the invention.

With the device of the invention assembled in the manner shown in FIGS. 1 through 3 and with housing connected to base 22a as by sonic welding using energy directors 31 (FIG. 5), the first step in preparing the device for use is filling of the ullage reservoirs with the ullage-defining means. This is accomplished using a conventional syringe, the filling needle of which is inserted into an inlet port 78 formed in cover assembly 44 (FIGS. 2 and 7). During the ullage reservoir filling step, air contained within the reservoirs is vented through vent 80 (FIGS. 2 and 7). Referring particularly to FIGS. 3 and 14, it is to be noted that cover 50 of cover assembly 44 is provided with a centrally disposed cavity 58 which overlays the central portion of distendable membrane 40 and cooperates therewith to form the central conformable ullage reservoir 48 (FIGS. 3 and 14). During the ullage reservoir filling step, the ullage defining means, in this case a flowable mass such as a viscous oil "CU", flows from inlet port 78 through flow channel 85 and into central conformable ullage reservoir 48 (FIG. 7). As best seen in FIG. 14, this causes the central portion of distendable membrane 40a along with the central portion of barrier membrane 49 to distend downwardly in a direction toward the upper, concave surface 30a of member 30 of base assembly 22. It is important to note that this downward extension of the central portion of the membrane causes a buildup of internal stresses in this portion of the membrane which mitigates against its ability to return to its starting position following filling of the medicament reservoir in a manner presently to be discussed.

Referring particularly to FIGS. 2 and 7, it is to be noted that central ullage reservoir 48 and peripheral ullage reservoir 46 are connected by first and second passageways 84 and 86 formed in cover member 50. In a manner presently to be described, the viscous oil, which forms the ullage defining means of the present embodiment of the invention, can flow into and out of central ullage reservoir 48 both during the medicinal reservoir filling step and also during the infusion step during which the medicinal fluid is infused into the patient. The details of this unique aspect of the invention will presently be described. As shown in FIG. 14, simultaneously with filling of central ullage reservoir 48 is the filling of the generally toroidal-shaped, conformable ullage reservoir 46 via fluid flow passageway 86. Filling of ullage reservoir 46 causes the peripheral portion of distendable membrane 40 to distend downwardly toward elastomeric insert 52 which is formed in base assembly 22.

Figure 9:
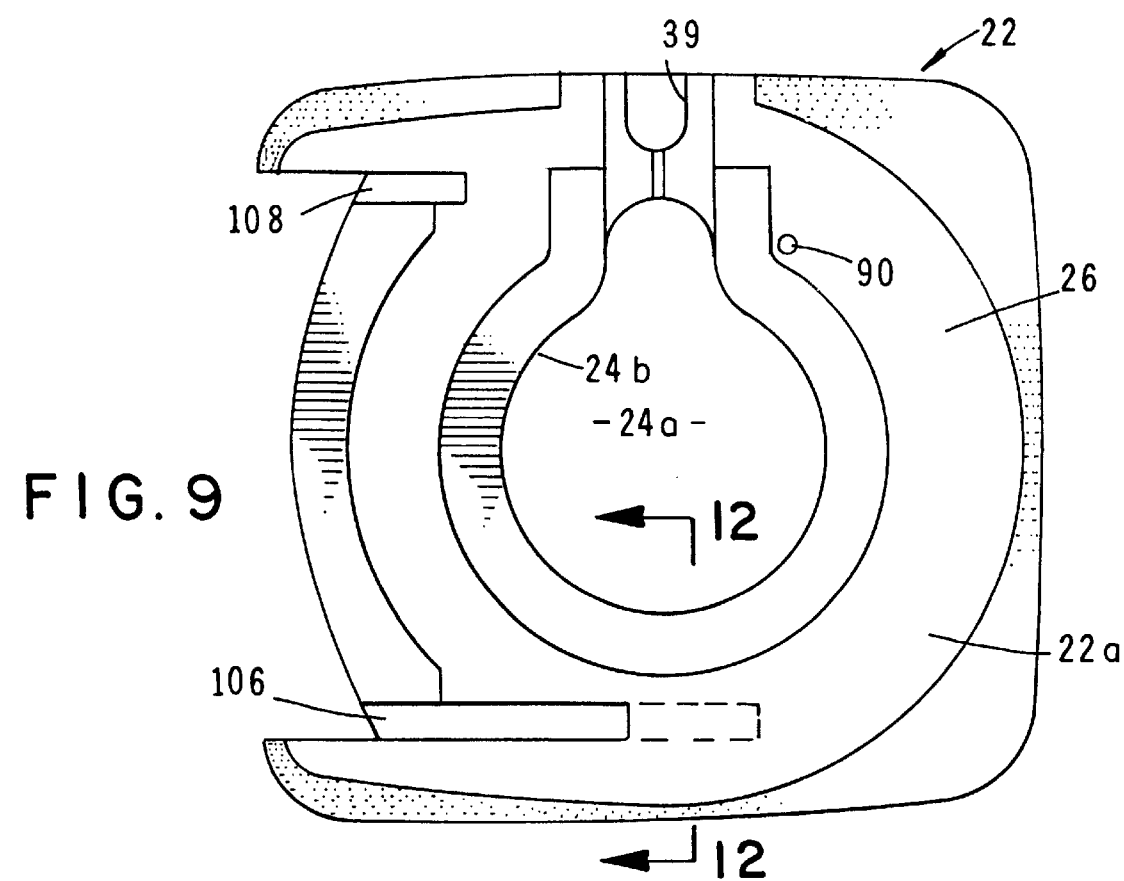
FIG. 9 is a view taken along lines 9—9 of FIG. 5.

The next step in readying the device of the invention for use is the fluid indicator reservoir filling step wherein an appropriate indicator fluid such as a colored oil is caused to flow into reservoir 42. This colored oil, which is designated in FIG. 14 by the numeral 42*a*, can comprise several types of oil including peanut oil. Fluid indicator reservoir 42 is filled with the indicator fluid 42*a* using conventional syringe of the character having a pierceable needle which is inserted into a fill port 90 formed in base assembly 22 (FIG. 9).

With the central and peripheral ullage reservoirs filled with the flowable mass "CU" which comprises the ullage defining means of the invention and with fluid indicator reservoir 42 filled with an appropriate indicator fluid 42*a*, the next step in preparing the device for use is the filling of the medicinal fluid reservoir 32. This is accomplished using the previously mentioned fill means of the invention which here comprises the filling syringe 38. As best seen by referring to FIG. 16, filling syringe 38, which is of conventional construction, includes a hollow piercing cannula 38*a*. When the fill means of the invention is interconnected with the fluid delivery portion of the device via fill opening 39 in the manner illustrated in FIGS. 15 and 16, piercing cannula 38*a* will pierce septum 36 and permit the flow medicinal fluid from the fluid reservoir of the syringe assembly 38 into the inlet port 34 of the medicinal fluid reservoir 32. Filling of reservoir 32 with the medicinal fluid causes the barrier membrane 49 to exert forces against the central portion of distendable membrane 40, which has previously been prestressed during filling of the ullage reservoir, causing it to distend upwardly in a direction toward cover member 50. Uniquely, as the barrier membrane and distendable membrane distend upwardly, the viscous oil "CU" which comprises the ullage-defining means which can range from centipoise one to greater than centipoise one-hundred of the invention will be caused to flow through passageway 86 from central reservoir 48 into peripheral reservoir 46. A comparison of FIGS. 14 and 16 shows that, as the flowable mass "CU" flows from central reservoir 48 toward peripheral reservoir 46, the indicator fluid disposed within peripheral reservoir 42 will be urged outwardly of the reservoir and, in a manner presently to be described, will flow into the indicator means of the invention.

Referring now to FIGS. 13A, 13B, 18A, 18B, and 18C, the construction of the novel indicator means of the present invention is there shown. This indicator means functions to indicate the flow of medicinal fluid from central medicinal fluid reservoir 32 outwardly of the device through the infusion means. In the present form of the invention, this important indicator means comprises an indicator lens assembly 94 which is interconnected with base assembly 22 to form the completed fluid delivery portion of the device shown in FIG. 1. Indicator lens assembly 94 includes a body portion 96 (FIGS. 18A and 18B) within which is formed a circuitous indicator fluid flow path 98. This circuitous fluid flow path comprises a plurality of interconnected, generally U-shaped flow passageways 98*a* which are disposed in close proximity along the length of body portion 96. When these passageways are viewed through the indicator lens 100, they appear as a series of spaced apart parallel lines.

Figure 8:
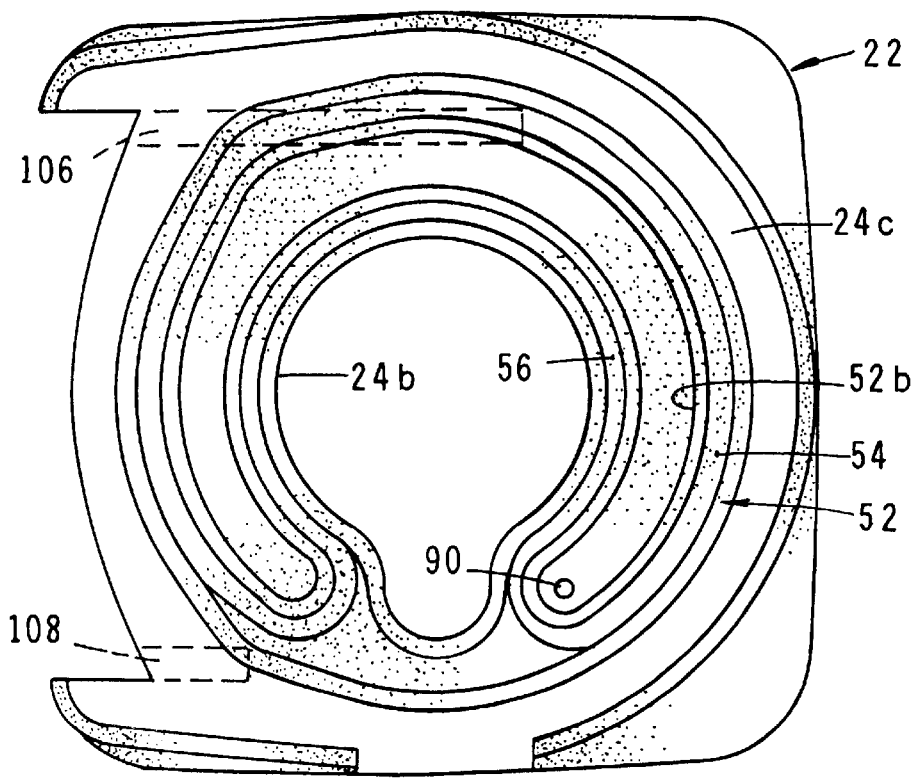
FIG. 8 is a view taken along lines 8—8 of FIG. 5.

As shown in FIG. 13A, an indicator fluid pick-up means or tube 102 is provided proximate one end of back plate 95, while a vent means shown here as a porous gas vent 104 is provided proximate the opposite end of back plate 95. As best seen by referring to FIGS. 8 and 12, base assembly 22 is provided with an elongated bore 106 which receives pick-up tube assembly 102 in a manner to place the pick-up tube in communication with peripheral fluid indicator reservoir 42. Similarly, base assembly 22 is provided with a bore 108 which is adapted to receive porous gas vent assembly 104 so that the assembly can communicate with atmosphere to enable appropriate venting of the indicator lens assembly during the indicator oil filling step.

Figure 16:
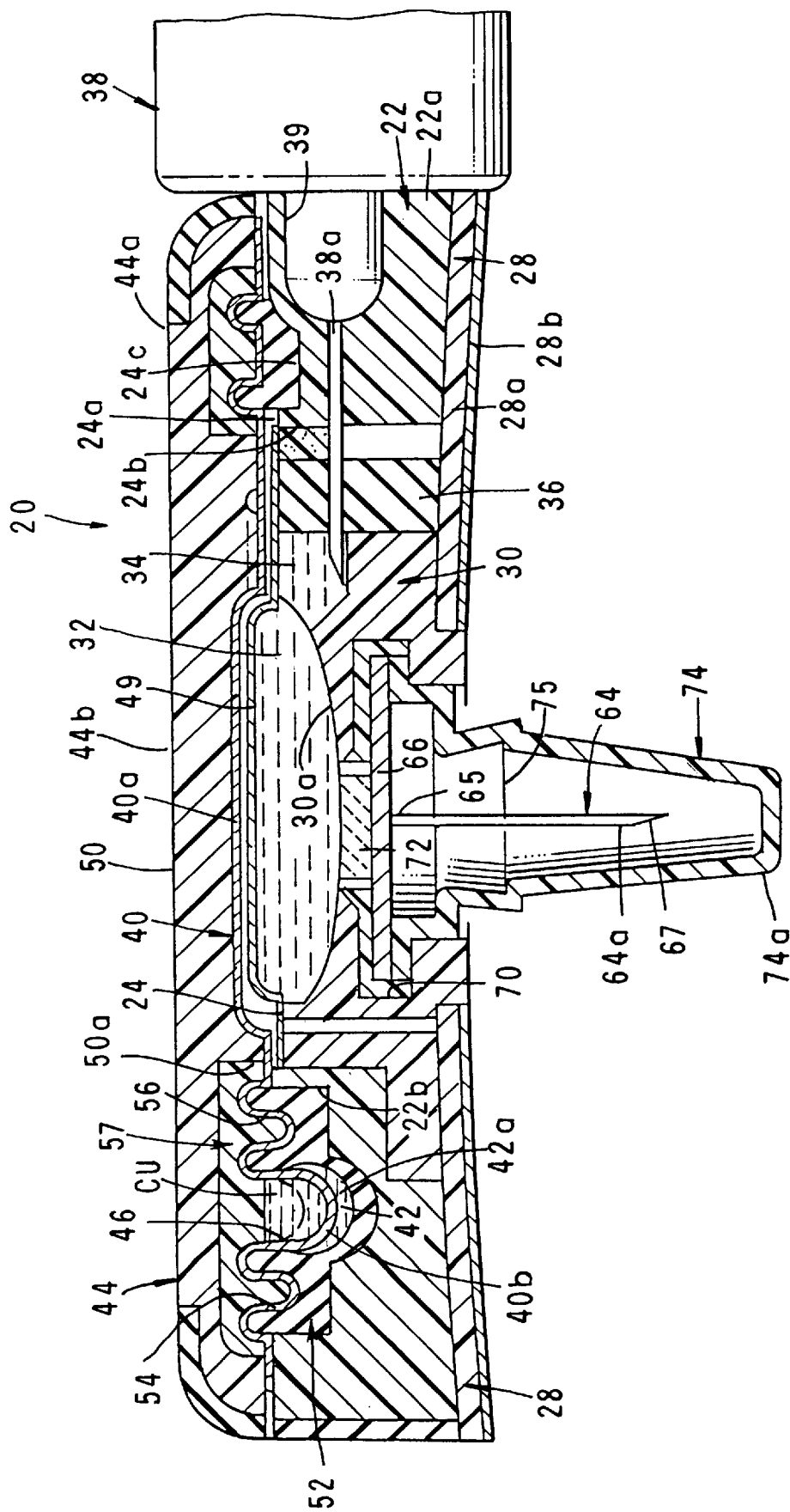
FIG. 16 is a side-elevational, partly cross-sectional view showing the fill means interconnected with the fluid delivery portion of the device and showing the reservoirs of the device filled with the medicinal fluid to be infused into the patient.

With the indicator lens assembly assembled with the base assembly 22 in the manner thus described, filling of medicinal fluid reservoir 32 with the medicinal fluid in the manner shown in FIG. 16 will cause displacement of the flowable mass or ullage oil into peripheral ullage reservoir 46. This flow of the ullage defining means into reservoir 46 will, in turn, displace the indicator fluid from indicator fluid reservoir 42 causing it to flow through pick-up tube 102 and into circuitous fluid passageway 98 which is in fluid communication therewith. As the indictor fluid flows through passageway 98, air within the passageway will be vented to atmosphere via vent assembly 104. The quantity of indicator fluid contained within indicator fluid reservoir 42 is such that upon completion of the filling of medicinal reservoir in the manner shown in FIG. 16, passageway 98 of the indicator lens assembly will be completely filled. Accordingly, when the indicator body is viewed through indicator lens 100, a series of parallel, brightly colored lines will appear to the viewer.

With the various reservoirs of the device filled in the manner shown in FIG. 16, the device is in condition for use in infusing medicinal fluid into the patient. This is accomplished by breaking away of protective shroud 74 so as to expose cannula 64 and by removing the lower peel strip 28*b* of the pad assembly 28. A downward pressure exerted on the device will then cause infusion cannula 64 to pierce the skin and tissue of the patient and to bring the lower adhesive covered surface of the pad assembly into contact with the patient's skin so as to securely interconnect the device with the patient during the infusion step.

Figure 7A:
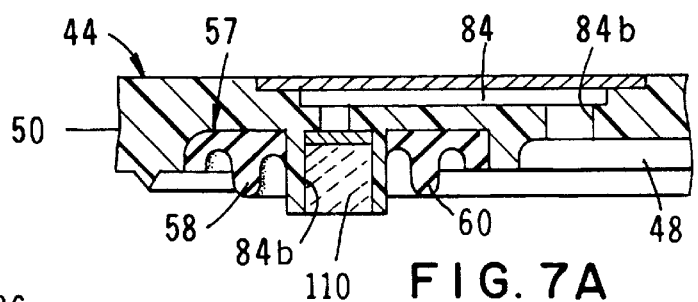
FIG. 7A is a cross-sectional view taken along lines 7A—7A of FIG. 7.

Flow of medicinal fluid from chamber 32 into the patient via cannula 64 is controlled by the several flow control means of the invention. These important flow control means will now be described. The first of these novel flow control means is carried by cover assembly 44 and functions to permit the viscous oil "CU" which comprises the ullage defining means of the invention to flow in a first direction from central conformable ullage reservoir 48 toward generally toroidal shaped conformable ullage reservoir 46 via first fluid passageway 84 formed in cover member 50 (FIG. 2). This first flow control means is here provided in the form of a one-way valve means or valve 110 (FIGS. 2, 7 and 7A). This novel one-way valve 110, which is housed within port 84*a* of passageway 84, permits the ullage medium or viscous oil "CU" to flow in a first direction from central ullage reservoir 48 toward peripheral reservoir 46 via port 84*b* (FIG. 7), but prevents flow of the ullage oil in the opposite direction.

Figure 7B:
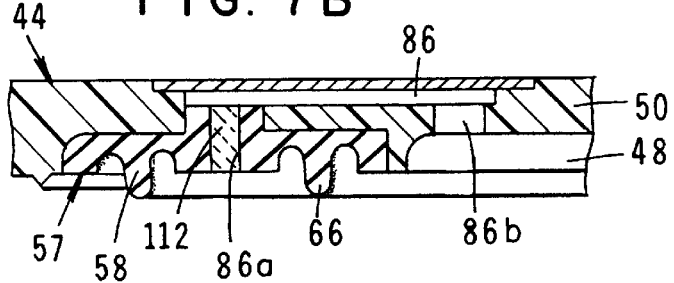
FIG. 7B is a cross-sectional view taken along lines 7B—7B of FIG. 7.

The second important flow control means of the invention comprises a flow rate control means carried by cover assembly 44 for controlling the rate of flow of the ullage defining means or ullage oil "CU" between generally toroidal shaped conformable ullage reservoir 46 and central conformable ullage reservoir 48 via second passageway 86 (FIG. 2). This important flow rate control means is here provided in the form of a rate control frit 112 which, as best seen in FIGS. 2, 7 and 7B, is mounted within a port 86a of passageway 86 so as to control the rate of flow of the ullage oil from peripheral ullage reservoir 46 back toward central ullage reservoir 48 via port 86b (FIG. 7B). In this regard, it is to be understood that as the medicinal fluid is dispensed from medicinal fluid reservoir 32 due to the urging of the peripheral portion 40b of elastomeric membrane 40 which tends to return from its distended position shown in FIG. 16 to its starting position shown in FIGS. 3 and 4, the ullage oil "CU" contained within peripheral reservoir 46 will be urged to flow back toward central reservoir 48 via passageway 86 to fill the negative pressure void left in reservoir 48 as the distendable membrane moves downwardly toward base assembly 22. Simultaneously, the colored indicator oil 42a filling fluid passageway 98 of the indicator lens assembly will be urged to flow from body portion 96 of the assembly back toward indicator reservoir 42. This flow of indicator oil from passageway 98 will, of course, be proportional to the flow of medicinal fluid outwardly of the device from medicinal fluid reservoir 32. When the indicator oil is viewed through indicator lens 100, the user will see a progressive emptying of the colored lines defined by circuitous flow passageway 98 from one side of the lens to the other indicating not only that fluid is flowing from medicinal reservoir 32, but also indicating the amount of fluid remaining in the reservoir and the rate of flow of fluid therefrom. Stated another way, when the medicinal reservoir is full, lines 98a will appear red in color along the entire length of the viewing lens. However, as the reservoir empties a progressively fewer number of the lines will appear red in color much in the same manner as a gasoline gage in an automobile.

Still another flow control means of the invention comprises a second fluid flow control means which is carried by base assembly 22 for restricting the flow of medicinal fluid from central medicinal fluid reservoir 32 toward inlet 65 of piercing cannula 64. This second flow control means is here provided in the form of the previously identified impedance frit 72 for control of environmental perturbations such as shock and vibration. As previously discussed, impedance frit 72, which is disposed between the outlet of reservoir 32 and the inlet 65 of cannula 64, can be constructed of various materials, but a material such as stainless steel, porous plastic or porous ceramic which is readily available from numerous sources well known to those skilled in the art has proven suitable for the intended use.

Figure 17:
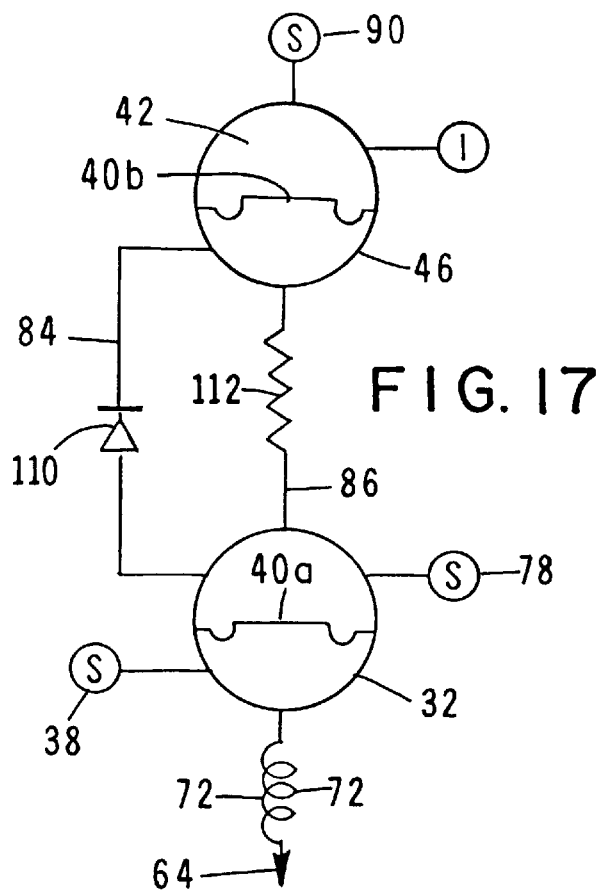
FIG. 17 is a generally diagrammatic view illustrating the operation of the flow indicator means of the invention.
Figure 18A:
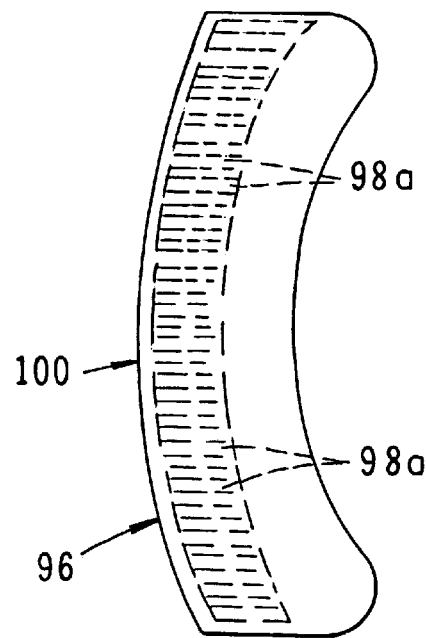
FIG. 18A is a top plan view of the flow indicator lens of the invention.
Figure 18B:
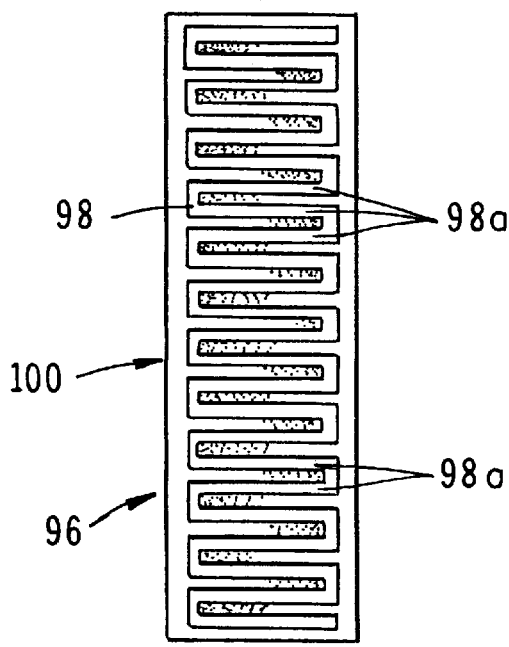
FIG. 18B is a front view of the flow indicator lens.
Figure 18C:
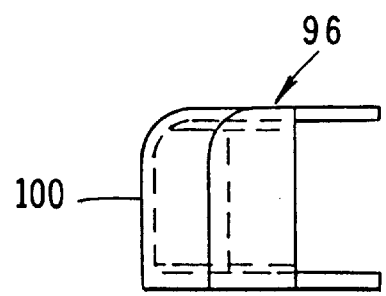
FIG. 18C is a right side elevational view of the flow indicator lens shown in FIG. 18A.

Turning now to FIG. 17, a diagrammatic representation of the flow paths of the various fluids contained within the device of the invention is there illustrated. Starting at the lower portion of the FIG. 17, the needle of assembly 64 and impedance frit 72 are shown interconnected with medicinal fluid reservoir 32. Reservoir 32 can be filled in the manner described using the fill means or fill assembly generally designated by the numeral 38. Disposed between central ullage reservoir 48 and medicinal fluid reservoir 32 is the central portion of the stored energy means or the central portion 40a of the distendable membrane 40. Flow of the ullage medium, in this case a flowable mass such as viscous oil "CU", is flowable from central ullage reservoir 48 to peripheral ullage reservoir 46 via one-way valve 110 which controls fluid flow through first flow passageway 84 formed in cover member 50. Separating toroidal shaped ullage reservoir 48 and indicator fluid reservoir 42 is the peripheral portion 40b of the distendable membrane 40. In the manner previously described, indicator fluid reservoir 42 can be filled with indicator fluid 42a via fill port 90. Interconnected with indicator fluid reservoir 42 via indicator tube assembly 102 is circuitous flow passageway 98 of body 96 of the indicator means "I" of the invention. Finally, the novel flow rate control means of the invention, or frit 112, is disposed within second passageway 86 formed in cover member 50. With this novel construction as the medicinal fluid reservoir 32 is filled, membrane portion 40a will be distended in a manner to cause the ullage contained in central reservoir 48 to flow into peripheral reservoir 46 via passageway 84 and one-way valve means 110. This will, in turn, cause the peripheral portion 40b of the distendable membrane 40 to urge the indicator fluid contained within reservoir 42 outwardly thereof via tube assembly 102 into passageway 98 formed in indicator body 96. This outward flow of indicator fluid will fill passageway 98 indicating a filled condition of the medicinal fluid reservoir when the indicator body is viewed through indicator lens 100. However, when the medicinal fluid is dispensed from reservoir 32 to the patient due to the flow of the ullage oil "CU" contained in peripheral reservoir 46 into the central reservoir 48 the indicator oil will be urged to flow outwardly of circuitous passageway 98 in a direction back toward indicator fluid reservoir 42. As the brightly colored indicator oil flows outwardly of indicator body 96, the body as viewed through indicator lens 100 will evidence a continued decrease in the number of lines viewed through indicator lens 100 which evidence the red color. This decrease in the lines showing color will indicate not only that fluid is flowing from medicinal reservoir 32, but will also indicate the rate of such flow and the amount of fluid remaining within the fluid reservoir.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A device for infusing medicinal fluid into a patient at a controlled rate comprising:
   (a) a base assembly;
   (b) a cover assembly superimposed over and sealably connected to said base assembly, said cover assembly having first and second fluid passageways;
   (c) a stored energy means comprising a distendable membrane disposed intermediate said base assembly and said cover assembly, said distendable membrane being distendable from a first configuration to a second configuration and, when distended into said second configuration, having a tendency to return to its first configuration, said distendable membrane:
      (i) forming in conjunction with said base assembly a medicinal fluid reservoir having an inlet and an indicator fluid reservoir; and
      (ii) forming in conjunction with said cover assembly a central ullage reservoir and a peripheral ullage reservoir, said central ullage reservoir and said peripheral ullage reservoir being interconnected by said first and second fluid passageways;
   (d) an ullage defining means for providing ullage within said central ullage reservoir and within said peripheral ullage reservoir, said ullage defining means comprising a flowable mass flowable between said central ullage reservoir and said peripheral ullage reservoir via said first and second passageways formed in said cover assembly;

(e) indicator fluid provided within said indicator fluid reservoir;

(f) fill means communicating with said base assembly for filling said medicinal fluid reservoir with the medicinal fluid to be infused into the patient;

(g) infusion means for infusing medicinal fluid from said medicinal fluid reservoir into the patient, said infusion means comprising a hollow cannula connected to said base assembly, said hollow cannula having:
  (i) an inlet in communication with said medicinal fluid reservoir; and
  (ii) an outlet end provided in the form of a pierceable portion extending outwardly from said base assembly for insertion into the patient; and (h) indicator means interconnected with said base assembly for indicating the flow of medicinal fluid from said central medicinal fluid reservoir outwardly toward the patient.

2. A device as defined in claim 1 in which said indicator means comprises an indicator lens assembly connected to one of said base assembly and said cover assembly, said indicator lens assembly including:
  (a) a body portion having a circuitously shaped indicator fluid flow path; and
  (b) pick-up means connected to said body portion, said pick-up means being in communication with said indicator fluid reservoir for causing indicator fluid to flow into and out of said circuitously shaped indicator fluid flow path in response to said flowable mass flowing between said peripheral ullage reservoir and said central ullage reservoir.

3. A device as defined in claim 1 further including first flow control means carried by said cover assembly for permitting said flowable mass to flow in a first direction from said central conformable ullage reservoir toward said peripheral ullage reservoir via said first passageway upon filling of said medicinal fluid reservoir by said fill means, but positively preventing said flowable mass from flowing in an opposite direction.

4. A device as defined in claim 1 further including flow rate control means carried by said cover assembly for controlling the rate of flow of said flowable mass between said peripheral ullage reservoir and said central ullage reservoir via said second passageway.

5. A device as defined in claim 1 further including second flow control means carried by said base assembly for controlling flow of medicinal fluid from said medicinal fluid reservoir toward said inlet of said hollow cannula.

6. A device as defined in claim 1 in which said base assembly comprises:
  (a) a base component having a central opening; and
  (b) a medicinal fluid reservoir defining housing receivable within said central opening of said base component.

7. A device as defined in claim 1 in which said base assembly further includes a peripheral portion, and a first elastomeric insert disposed in said peripheral portion of said base assembly, said first elastomeric insert having at lease one circumferentially extending groove formed therein.

8. A device as defined in claim 7 in which said cover assembly further includes a peripheral portion, and a second elastomeric insert disposed in said peripheral portion, said second elastomeric insert having at least one circumferentially extending protuberance sealably receivable within said groove formed in said first elastomeric insert.

9. A device as defined in claim 7 in which said fill means comprises a syringe assembly having a piercing cannula and in which said base assembly further includes a septum disposed proximate said inlet of said medicinal fluid reservoir, said septum being pierceable by said piercing cannula of said syringe assembly.

10. A device for use in infusing medicinal fluid into a patient at a controlled rate comprising:
  (a) a base assembly having an upper surface and a lower surface, said base assembly including a central portion, a peripheral portion circumscribing said central portion, said peripheral portion having a generally toroidal shaped chamber formed therein;
  (b) stored energy means for forming in conjunction with said central portion of said base, a medicinal fluid reservoir having an inlet and an outlet and for forming in conjunction with said toroidal shaped chamber, a generally toroidal shaped indicator fluid reservoir having an inlet and an outlet, said stored energy means comprising at least one distendable membrane superimposed over said upper surface of said base assembly, said membrane having a central portion overlaying said central portion of said base assembly and a peripheral portion overlaying said toroidal shaped chamber, said peripheral portion being distendable from a first configuration to a second configuration to establish internal stresses, said stresses tending to move said membrane toward said first configuration;
  (c) a cover assembly sealably interconnected with said base assembly, said cover assembly having a central portion overlaying said central portion of said base assembly and a peripheral portion overlaying said generally toroidal shaped chamber formed in said base assembly for forming in conjunction with said membrane a generally toroidal shaped, conformable ullage reservoir having a first inlet port, said central portion having a central chamber for forming in conjunction with said membrane a central conformable ullage reservoir, having a first inlet port, said central conformable ullage reservoir being in fluid communication with said generally toroidal shaped, conformable ullage reservoir via first and second passageways formed in said cover;
  (d) an ullage defining means for providing ullage within said central conformable ullage reservoir and within said generally toroidal shaped conformable ullage reservoir, said ullage defining means comprising a flowable mass flowable between said central conformable ullage reservoir and said generally toroidal shaped, conformable ullage reservoir via said first and second passageways formed in said cover assembly;
  (e) indicator fluid provided within said generally toroidal shaped indicator fluid reservoir;
  (f) fill means communicating with said base assembly for filling said medicinal fluid reservoir;
  (g) infusion means for infusing medicinal fluid from said medicinal fluid reservoir into the patient, said infusion means comprising a hollow cannula connected to said base assembly, said hollow cannula having:
    (i) an inlet in communication with said medicinal fluid reservoir; and
    (ii) an outlet end provided in the form of a pierceable portion extending outwardly from said base assembly for insertion into the patient; and (h) indicator means interconnected with said base assembly for indicating the flow of medicinal fluid from said medicinal fluid reservoir toward the patient.

11. A device as defined in claim 10 in which said indicator means comprises an indicator lens assembly having:

(a) a body portion connected to said base assembly, said body portion having circuitously shaped indicator fluid flow path; and (b) a pick-up means connected to said body portion, said pick-up means being in communication with said generally toroidal shaped indicator fluid reservoir for causing indicator fluid to flow into and out of said circuitously shaped indicator fluid flow path in response to said flowable mass flowing between said generally toroidal shaped, conformable ullage reservoir and said central conformable ullage reservoir.

12. A device as defined in claim 10 further including first flow control means carried by said cover assembly for permitting said flowable mass to flow in a first direction from said central conformable ullage reservoir toward said generally toroidal shaped conformable ullage reservoir via said first passageway upon filling of said medicinal fluid reservoir by said fill means, but positively preventing said flowable mass from flowing in an opposite direction.

13. A device as defined in claim 10 further including flow rate control means carried by said cover assembly for controlling the rate of flow of said flowable mass between said generally toroidal shaped, conformable ullage reservoir and said central conformable ullage reservoir via said second passageway.

14. A device as defined in claim 10 further including second flow control means carried by said base assembly for controlling flow of medicinal fluid from said medicinal fluid reservoir toward said inlet of said hollow cannula.

15. A device for use in infusing medicinal fluid into a patient at a controlled rate comprising:

(a) a base assembly having an upper surface and a lower surface, said base assembly including a central portion, a peripheral portion circumscribing said central portion, said peripheral portion having a generally toroidal shaped chamber formed therein;

(b) stored energy means for forming in conjunction with said central portion of said base, a medicinal fluid reservoir having an inlet and an outlet and for forming in conjunction with said toroidal shaped chamber, a generally toroidal shaped indicator fluid reservoir having an inlet and an outlet, said stored energy means comprising at least one distendable membrane superimposed over said upper surface of said base assembly, said membrane having a central portion overlaying said central portion of said base assembly and a peripheral portion overlaying said toroidal shaped chamber, said peripheral portion being distendable from a first configuration to a second configuration to establish internal stresses, said stresses tending to move said membrane toward said first configuration;

(c) a cover assembly sealably interconnected with said base assembly, said cover assembly having a central portion overlaying said central portion of said base assembly and a peripheral portion overlaying said generally toroidal shaped chamber formed in said base assembly for forming in conjunction with said membrane a generally toroidal shaped, conformable ullage reservoir having a first inlet port, said central portion having a central chamber for forming in conjunction with said membrane a central conformable ullage reservoir, having a first inlet port, said central conformable ullage reservoir being in fluid communication with said generally toroidal shaped, conformable ullage reservoir via first and second passageways formed in said cover;

(d) an ullage defining means for providing ullage within said central conformable ullage reservoir and within said generally toroidal shaped conformable ullage reservoir, said ullage defining means comprising a flowable mass flowable between said central conformable ullage reservoir and said generally toroidal shaped, conformable ullage reservoir via said first and second passageways formed in said cover assembly;

(e) indicator fluid provided within said generally toroidal shaped indicator fluid reservoir;

(f) fill means communicating with said base assembly for filling said medicinal fluid reservoir;

(g) infusion means for infusing medicinal fluid from said medicinal fluid reservoir into the patient, said infusion means comprising a hollow cannula connected to said base assembly, said hollow cannula having:

(i) an inlet in communication with said medicinal fluid reservoir; and (ii) an outlet end provided in the form of a pierceable portion extending outwardly from said base assembly for insertion into the patient; and (h) indicator means for indicating the flow of medicinal fluid from said medicinal fluid reservoir toward the patient; said indicator means comprising an indicator lens assembly having:

(i) a body portion connected to said base assembly, said body portion having circuitously shaped indicator fluid flow path; and (ii) a pick-up means connected to said body portion, said pick-up means being in communication with said generally toroidal shaped indicator fluid reservoir for causing indicator fluid to flow into and out of said circuitously shaped indicator fluid flow path in response to said flowable mass flowing between said generally toroidal shaped, conformable ullage reservoir and said central conformable ullage reservoir.

16. A device as defined in claim 15 further including first flow control means carried by said cover assembly for permitting said flowable mass to flow in a first direction from said central conformable ullage reservoir toward said generally toroidal shaped conformable ullage reservoir via said first passageway upon filling of said medicinal fluid reservoir by said fill means, but positively preventing said flowable mass from flowing in an opposite direction.

17. A device as defined in claim 15 further including flow rate control means carried by said cover assembly for controlling the rate of flow of said flowable mass between said generally toroidal shaped, conformable ullage reservoir and said central conformable ullage reservoir via said second passageway.

18. A device as defined in claim 15 further including second flow control means carried by said base assembly for controlling flow of medicinal fluid from said medicinal fluid reservoir toward said inlet of said hollow cannula.

19. A device as defined in claim 15 in which said ullage defining means comprises a viscous oil.

20. A device as defined in claim 15 in which said ullage defining means comprises a flourinated oil.

21. A device as defined in claim 15 in which said indicator fluid comprises a colored oil.

22. A device as defined in claim 15 in which said fill means comprises a syringe assembly having a piercing cannula and in which said base assembly further includes a septum disposed proximate said inlet of said medicinal fluid reservoir, said septum being pierceable by said piercing cannula of said syringe assembly.

23. A device as defined in claim 15 in which said base assembly further includes a first elastomeric insert disposed in said peripheral portion of said base assembly, said first elastomeric insert having at least one circumferentially extending groove formed therein.

24. A device as defined in claim 23 in which said cover assembly further includes a second elastomeric insert disposed in said peripheral portion of said cover assembly, said second elastomeric insert having at least one circumferentially extending protuberance sealably receivable within said groove formed in said first elastomeric insert.

* * * * *